(12) United States Patent
Matsubara et al.

(10) Patent No.: US 10,165,776 B2
(45) Date of Patent: Jan. 1, 2019

(54) SUBSTITUTED PYRAZOLYLPYRAZOLE DERIVATIVE AND USE OF SAME AS HERBICIDE

(71) Applicant: KYOYU AGRI CO., LTD., Kanagawa (JP)

(72) Inventors: Ken Matsubara, Nagano (JP); Makoto Niino, Nagano (JP)

(73) Assignee: KYOYU AGRI CO., LTD., Kanagawa (JP)

( * ) Notice: Subject to any disclaimer, the term of this patent is extended or adjusted under 35 U.S.C. 154(b) by 0 days.

(21) Appl. No.: 15/541,117

(22) PCT Filed: Jan. 22, 2016

(86) PCT No.: PCT/JP2016/051832
§ 371 (c)(1),
(2) Date: Jun. 30, 2017

(87) PCT Pub. No.: WO2016/117679
PCT Pub. Date: Jul. 28, 2016

(65) Prior Publication Data
US 2017/0367335 A1  Dec. 28, 2017

(30) Foreign Application Priority Data
Jan. 23, 2015 (JP) ................................. 2015-011041

(51) Int. Cl.
| | |
|---|---|
| *C07D 471/04* | (2006.01) |
| *C07D 487/04* | (2006.01) |
| *A01N 43/90* | (2006.01) |
| *A01N 43/56* | (2006.01) |
| *A01N 29/04* | (2006.01) |
| *A01N 33/18* | (2006.01) |

(52) U.S. Cl.
CPC ............. *A01N 43/56* (2013.01); *A01N 29/04* (2013.01); *A01N 33/18* (2013.01); *A01N 43/90* (2013.01); *C07D 471/04* (2013.01); *C07D 487/04* (2013.01)

(58) Field of Classification Search
CPC ...... A01N 43/90; A01N 43/56; C07D 231/16; C07D 471/04; C07D 487/04
See application file for complete search history.

(56) References Cited

U.S. PATENT DOCUMENTS

| | | | |
|---|---|---|---|
| 5,167,691 A | 12/1992 | Maravetz | |
| 5,262,382 A | 11/1993 | Maravetz | |
| 5,580,986 A | 12/1996 | Dorfmeister et al. | |
| 5,756,424 A * | 5/1998 | Dorfmeister ........... | A01N 43/56 504/246 |
| 5,869,686 A | 2/1999 | Dorfmeister et al. | |
| 2016/0152622 A1 | 6/2016 | Matsubara et al. | |

FOREIGN PATENT DOCUMENTS

| | | |
|---|---|---|
| JP | 8-506086 | 7/1996 |
| WO | 94/08999 | 4/1994 |
| WO | 2015/020156 | 2/2015 |

OTHER PUBLICATIONS

Miyahara, "Ecology of Paddy Weeds and their Control—Explanation of Weeds of Rice Paddy Crops and Herbicide", Zenkoku Noson Kyoiku Kyokai, p. 159, First Edition Published Dec. 15, 1992, with Partial English Translation.
International Search Report dated Mar. 22, 2016 in International (PCT) Application No. PCT/JP2016/051832.

* cited by examiner

*Primary Examiner* — John Pak
(74) *Attorney, Agent, or Firm* — Wenderoth, Lind & Ponack, L.L.P.

(57) ABSTRACT

Provided is a compound capable of effectively control worst weeds of higher leaf stages that present practical problems. A specific pyrazolylpyrazole derivative of formula (I) is disclosed that is able to solve the above-mentioned problems.

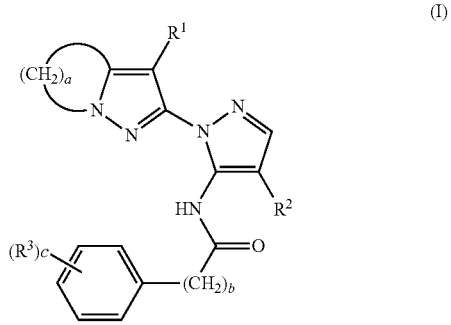

(I)

12 Claims, No Drawings

SUBSTITUTED PYRAZOLYLPYRAZOLE DERIVATIVE AND USE OF SAME AS HERBICIDE

TECHNICAL FIELD

The present invention relates to a substituted pyrazolylpyrazole derivative and the use of that compound as a herbicide.

BACKGROUND ART

Numerous herbicides have recently come to be used in the cultivation of agricultural crops, and have contributed to reduced labor for farmers and improved productivity of agricultural crops. Numerous herbicides are also used practically in the cultivation of field and paddy rice.

However, there is considerable diversity in the species of weeds, the germination and growth periods of each species of weed are not uniform, and the growth of perennial weeds extends over a long period of time. Consequently, it is extremely difficult to control all weeds with a single spraying of herbicide.

Early to mid-term one-shot herbicides have been shown to be effective for paddy rice by treating during the second to third leaf stage of paddy weeds (generic term for *Echinochloa oryzicola*, *Echinochloa crus-galli* var. *crus-galli*, *Echinochloa crus-galli* var. *formosensis*, *Echinochloa crus-galli* var. *praticola* and *Echinochloa crus-galli* var. *caudata*), and major weeds can be controlled by a single treatment (see Non-Patent Document 1). However, it is extremely difficult to control paddy weeds that have grown to the 3.5 leaf stage or more with early to mid-term one-shot herbicides currently in practical use, and the control of paddy weeds in the third leaf stage and control of paddy weeds in the 3.5 leaf stage are technically completely different.

Moreover, maintaining herbicidal effects (or residual activities) over a long period of time is important in terms of reducing spraying of agricultural chemicals, saving on labor and curtailing costs, and is considered to be an essential area of performance for early to mid-term one-shot herbicides.

In addition, acetolactate synthase (ALS) inhibitors have come to be widely used in recent years, and weeds exhibiting resistance to ALS inhibitors have become a problem. There are few herbicides demonstrating adequate efficacy against ALS inhibitor-resistant biotypes of the perennials of *Sagittaria trifolia* and *Sagittaria pygmeae*. In addition, examples of perennial weeds that have caused problems in recent years include *Eleocharis kuroguwai*, *Scirpus planiculmis* and *Scirpus nipponicus*, while examples of annuals include *Aeschynonmene indica*, *Leptochloa chinensis* and *Murdannia keisak*, and there are few herbicides that demonstrate adequate efficacy against these difficult-to-control weeds.

On the other hand, numerous pyrazole derivatives are used practically as herbicides, and although pyrazole derivatives such as 4-(2,4-dichlorobenzoyl)-1,3-dimethyl-5-pyrazolyl p-toluenesulfonate (common name: "Pyrazolate"), 2-[4-(2,4-dichlorobenzoyl)-1,3-dimethylpyrazol-5-yloxy] acetophenone (common name: "Pyrazoxyfen") or 2-[4-(2,4-dichloro-m-toluoyl)-1,3-dimethylpyrazol-5-yloxy]-4'-methylace tophenone (common name: "Benzofenap") are widely used, their registered application range for paddy weeds in Japan when used alone is up to the 1.5 leaf stage, and although these pyrazole derivatives are effective against a wide range of weeds, the efficacy thereof is not always adequate against paddy weeds of higher leaf stages.

In addition, although Compound 73 of Example 4 described in WO 94/08999 in the form of 1-(3-chloro-4,5,6,7-tetrahydropyrazolo[1,5-a]pyridin-2-yl) 5-[methyl(prop-2-ynyl)amino]pyrazole-4-carbonitrile (common name: "Pyraclonil") is effective against a wide range of weeds, its efficacy against paddy weeds of higher leaf stages is inadequate, and the registered application range in Japan against paddy weeds when using this herbicide alone is up to the 1.5 leaf stage.

Moreover, although WO 94/08999 also discloses compounds that demonstrate herbicidal effects by treating weeds that grow on farmland before and after growth, since there is no description regarding leaf stage, it cannot be said that these compounds have adequate effects against weeds of higher leaf stages. In addition, although isopropyl ammonium N-(phosphonomethyl) glycinate (common name: "Glyphosate Isopropylamine Salt"), for example, is widely used as a herbicide that demonstrates a wide range of effects against farmland weeds, problems have arisen in recent years regarding its efficacy against resistant weeds.

In addition, there has recently been growing concern over pollution of groundwater and rivers by pesticides. Consequently, there is a need for the development of herbicides that minimize effects on the environment such as by lowering the risk of runoff of active ingredients to locations other than locations of their intended application.

CITATION LIST

Patent Literature Document

Patent Document 1: WO 94/08999

Non-Patent Literature Document

Non-Patent Document 1: "Suiden Zasso no Seitai to Sono Bojo—Suitosaku no Zasso to Josozai Kaisetsu (Ecology of Paddy Weeds and their Control—Explanation of Weeds of Rice Paddy Crops and Herbicide)", p. 159

SUMMARY OF THE INVENTION

Technical Problem

An object of the present invention is to provide a compound that has superior characteristics as an herbicide ingredient, such as having a wide herbicidal spectrum including weeds that are resistant to existing herbicides, being able to control worst weeds of higher leaf stages that present practical problems, and not causing phytotoxicity to crops such as paddy rice.

Solution to Problem

As a result of conducting extensive studies to achieve the aforementioned object, the inventors of the present invention found that a pyrazolylpyrazole derivative having a specific chemical structure especially exhibits a wide herbicidal spectrum over a long period of time, demonstrates superior herbicidal efficacy against worst weeds of higher leaf stages, and has adequate safety with respect to cultivated crops, thereby leading to completion of the present invention on the basis of these findings. Thus, the present invention provides a pyrazolylpyrazole derivative in the form of a compound represented by the following formula (I):

[Chemical formula 1]

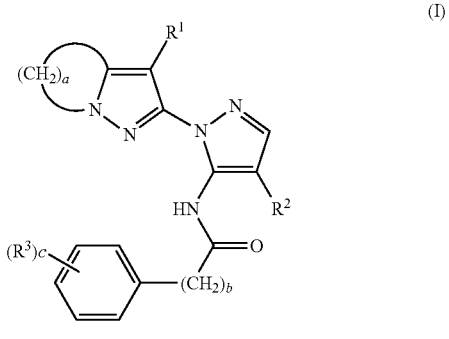

(I)

In the above formula, $R^1$ represents a chlorine atom or bromine atom, $R^2$ represents a cyano group or nitro group, $R^3$ may be substituted with a halogen atom, hydroxyl group, cyano group, nitro group depending on the case, $C_1$-$C_4$ alkyl group (which may be substituted with one or more halogen atoms depending on the case), or $C_1$-$C_4$ alkoxy group (which may be substituted with one or more halogen atoms depending on the case), a represents 3 to 5, b represents 1 to 3, and c represents 1 to 5, and each $R^3$ may be mutually the same or different when c is 2 or more.

Preferably, in formula (I), $R^1$ represents a chlorine atom, $R^2$ represents a cyano group, a represents 4, b represents 1, and c represents 1.

In the present description:

the mark "$C_a$-$C_b$" which is followed by a substituent means that the substituent has a to b carbon atoms.

Fluorine, chlorine, bromine and iodine atoms are included in "halogen atoms".

"Alkyl" as referring to a group per se or a moiety of a group can be linear or branched, and although there are no limitations thereon, examples thereof include methyl, ethyl, n- or isopropyl, n-, iso-, sec- or tert-butyl groups, and each is selected within a range of the specified number of carbon atoms thereof.

"Alkyl groups" may be groups in which at least one hydrogen atom contained in these groups is substituted with a halogen atom, examples in the case of an alkyl group include, but are not limited to, chloromethyl, dichloromnethyl, trifluoromethyl, chloroethyl, dichloroethyl, trifluoroethyl, tetrafluoropropyl, bromoethyl, bromopropyl and chlorobutyl groups, and are selected within a range of their respective specified number of carbon atoms.

"Alkoxy groups" refer to alkyl-O— groups in which the alkyl moiety is as previously defined, examples thereof include methoxy, ethoxy, n-propoxy, isopropoxy n-butoxy, isobutoxy, see-butoxy and tert-butoxy groups, and are selected within a range of their respective specified number of carbon atoms.

In the case where the aforementioned group or moiety is substituted with a plurality of halogen atoms, that group can be substituted with more than one halogen atoms that are the same or different.

In all of the formulas listed below, substituents and symbols have the same meanings as defined for formula (I) unless specifically defined otherwise. The compound of formula (I) provided by the present invention, wherein $R^3$ is a hydrogen atom, can easily be synthesized by an amidation reaction from a compound represented by formula (II).

[Chemical formula 2]

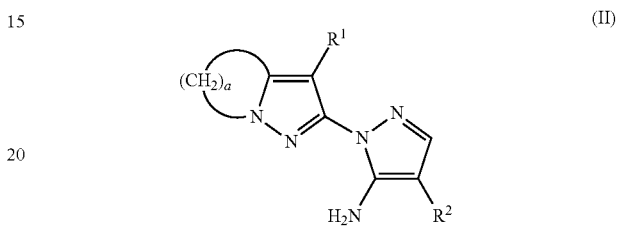

(II)

The compound of formula (II) can be synthesized from tetrahydro-2H-pyran-2-ylidene acetonitrile or 5-chlorovaleryl chloride according to the methods described in WO 93/10100 and WO 94/08999.

The amidation reaction of the compound of formula (II) per se can be carried out with reference to known reaction conditions (see, for example, WO 94/08999 and *Tetrahedron Lett.*, 32, 4019 (1991)).

The compound of formula (I) provided by the present invention has superior herbicidal efficacy and is useful as a herbicide as is clear from the results of the herbicidal activity tests described in Test Examples 1 to 4 to be subsequently described.

The compound of formula (I) of the present invention has activity against numerous types of crop weeds and non-crop weeds. Examples of cultivated plants include gramineous plants such as rice, wheat, barley, corn, oats or *sorghum*, broadleaf crops such as soybeans, cotton, beets, sunflowers or rapeseed, fruit trees, vegetables such as fruit vegetables, root vegetables or leafy vegetables, and grasses, and the compound of formula (I) can be used for the cultivation thereof.

The compound of the present invention has herbicidal efficacy against the various weeds listed below that cause problems in rice paddies in any of the treatment methods of soil treatment in an irrigated or unirrigated state, soil incorporation treatment and foliar treatment. Although the following lists examples thereof, these weeds are not limited to the following examples.

Examples of paddy weeds that can be controlled by the compound of formula (I) of the present invention include Alismataceous weeds such as *Alisma canaliculatum, Sagittaria trifolia* or *Sagittaria pygmaea*, Cyperaceous weeds such as *Cyperus difformis, Cyperus serotinus, Scirpus juncoides, Eleocharis kuroguwai, Scirpus planiculmis* or *Scirpus nipponicus*, Scrophulariaceous weeds such as *Lindernia procumbens, Lindernia dubia* subsp. *dubia* or *Lindernia dubia*, Pontederiaceous weeds such as *Monochoria vaginalis* or *Monochoria korsakowii*, Potamogetonaceous weeds such as *Potamogeton distinctus*, Lythraceous weeds such as *Rotala indica* or *Ammannia multifloa*, Asteraceous weeds such as *Bidens tripartita* or *Bidens frondosa*, Leguminoseous weeds such as *Aeschynomene indica*, Commelinaceous weeds such as *Murdannia keisak*, and Gramineous weeds such as *Echinochloa oryzicola, Echinochloa crus-galli* var. *crus-galli, Echinochloa crus-galli* var. *formosensis, Echinochloa crus-galli* var. *praticola, Echinochloa crus-galli* var. *caudata, Leptochloa chinensis, Leersia japonica, Paspalum distichum* or *Leersia oryzoides*.

In addition, the compound of the present invention has herbicidal efficacy against the various weeds listed below that cause problems in field land and non-crop land in any of the treatment methods of soil treatment, soil incorporation treatment and foliar treatment. Although the following lists examples thereof, these weeds are not limited to the following examples.

Examples thereof include broadleaf weeds, including Solanaceous weeds such as *Solanum nigrum* or *Datura stramonium*, Malvaceous weeds such as *Abutilon avicennae, Sida spinosa* or *Convolvulus arvensis*, Convolvulaceous weeds such as *Ipomoea pupurea*, Amaranthaceous weeds such as *Amaranthus lividus, Amaranthus retroflexus, Amaranthus palmeri* or *Amaranthus tuberculatus*, Asteraceous weeds such as *Xanthium struamarium, Ambrosia artemisiilifolia, Galinsoga ciliata, Cirsiumrn arvense, Senecio vulgaris, Stenactis annuus, Galinsoga parviflora, Sonchus arvensis, Sonchus oleiaceus* or *Matricaria indora*, Brassicaceous weeds such as *Rorippa indica, Sinapis arvensis, Capsella bursa-pastoris* or *Thiaspi arvense*, Polygonaceous weeds such as *Persicaria longiseta, Fallopia convolvulus, Polygonum aviculare* var. *condensatum, Polygonum aviculare* var. *monospeliense, Polygonum persicaria, Persicaria lapathifolia* var. *incana* or *Persicaria lapathifolia* var. *lapathifolia*, Portulacaceous weeds such as *Portulaca oleracea*, Chenopodiaceous weeds such as *Chenopodium album, Chenopodium ficifolium, Koclia scoparia* or *Atriplex patula*, Caryophyllaceous weeds such as *Stellaria media*, Scrophulariaceous weeds such as *Veronica persica*, Commelinaceous weeds such as *Commelina communis*, Lamiaceous weeds such as *Lamium amplexicaule, Lamium purpureum* or *Galeopsis tetrahit*, Euphorbiaceous weeds such as *Euphorbia supina* or *Euphorbia maculata*, Rubiaceous weeds such as *Galium spurium, Galium spurium* var. Echinospermon, *Rubia argyi* or *Galium aparine*, Violaceous weeds such as *Viola mandshurica* or *Viola arvensis*, Boraginaceous weeds such as *Myosotis arvensis*, and Leguminoseous weeds such as *Sesbania exaltata* or *Cassia obfusitolia*, and Gramineous weeds such as *Sorghum bicolor, Panicum dichotomiflorum, Sorghum halepense, Echinochloa crus-galli* var. *crus-galli, Digitaria ciliaris, Avena fatua, Eleusine indica, Setaria viridis, Alopecurus aequalis, Poa annua, Agropyron repens, Cynodon dactylon, Digitaria sanguinalis, Setaria pumila* or *Alopecurus myosuroides*, and Cyperaceous weeds such as *Cyperus rotundus*.

Moreover, the compound of the present invention is also able to control a wide range of weeds growing in mowed swaths, fallow land, orchards, grasslands, lawn grass plots, train line caps, vacant land and forest land, or on farm roads, causeways and other non-crop land.

Moreover, the compound of formula (I) of the present invention does not demonstrate phytotoxicity that becomes a problem for paddy rice in the case of any cultivation method such as direct seeding cultivation or transplantation cultivation of paddy rice.

The compound of formula (I) of the present invention can be applied before or after plant germination and can be mixed into soil before seeding.

Although the dosage of the compound of formula (I) of the present invention can be varied over a wide range corresponding to the type of compound, type of target plant, application window, location of application, properties of desired effects and the like, and as a general reference thereof, the dosage can be within the range of about 0.01 g to 100 g, and preferably about 0.1 g to 10 g, as the amount of active compound per are.

Although the compound of formula (I) of the present invention can be used alone, a formulation assistant and the like is normally incorporated in the compound of formula (I) in accordance with ordinary methods, and although there are no limitations thereon, it is preferably formulated and used in any arbitrary drug form such as a dustable powder, emulsifiable concentrate, oil miscible liquid, solubilizing agent, suspo-emulsion, fine granule, aerosol spray, less drifting dust, micro granules fine, fine grains F, granules, wettable powder, water dispersible granules, flowable concentrate, throw-in types (Jumbo), tablets, paste, emulsion in oil, water soluble powder, water soluble granules, soluble concentration or capsule suspension.

There are no limitations on formulation assistants able to be used for formulation, and examples include solid vehicles, liquid vehicles, binders, thickeners, surfactants, anti-freezing agents and preservatives.

Examples of solid vehicles include, but are not limited to, talc, bentonite, montmorillonite, clay, kaolin, calcium carbonate, sodium carbonate, sodium bicarbonate, mirabilite, zeolite, starch, acidic clay, diatomaceous earth, chaoite, vermiculite, slaked lime, vegetable powder, alumina, activated carbon, sugars, hollow glass, silica sand, ammonium sulfate and urea.

Examples of liquid vehicles include, but are not limited to, hydrocarbons (such as kerosene or mineral oil), aromatic hydrocarbons (such as toluene, xylene, dimethyl naphthalene or phenyl xylyl ethane), chlorinated hydrocarbons (such as chloroform or carbon tetrachloride), ethers (such as dioxane or tetrahydrofuran), ketones (such as acetone, cyclohexanone or isophorone), esters (such as ethyl acetate, ethylene glycol acetate or dibutyl maleate), alcohols (such as methanol, n-hexanol or ethylene glycol), polar solvents (such as N,N-dimethylformamide, dimethylsulfoxide or N-methylpyrrolidone) and water.

Examples of binders and thickeners include, but are not limited to, dextrin, sodium salts of carboxymethyl cellulose, polycarboxylic acid-based polymer compounds, polyvinylpyrrolidone, polyvinyl alcohol, sodium lignin sulfonate, calcium lignin sulfonate, sodium polyacrylate, gum arabic, sodium alginate, mannitol, sorbitol, bentonite-based mineral matter, polyacrylic acid and derivatives thereof, chaoite and natural sugar derivatives (such as xanthan gum or guar gum).

Examples of surfactants include, but are not limited to, anionic surfactants such as fatty acid salts, benzoates, alkylsulfosuccinates, dialkylsulfosuccinates, polycarboxylates, alkyl sulfate ester salts, alkyl sulfates, alkyl aryl sulfates, alkyl diglycol ether sulfates, alcohol sulfate ester salts, alkyl sulfonates, alkyl aryl sulfonates, aryl sulfonates, lignin sulfonates, alkyl diphenyl ether disulfonates, polystyrene sulfonates, alkyl phosphate ester salts, alkyl aryl phosphates, styryl aryl phosphates, polyoxyethylene alkyl ether sulfate ester salts, polyoxyethylene alkyl aryl ether sulfates, polyoxyethylene alkyl aryl ether sulfate ester salts, polyoxyethylene alkyl ether phosphates, polyoxyethylene alkyl aryl phosphate ester salts or salts of naphthalene sulfonate-formalin condensates, and nonionic surfactants such as sorbitan fatty acid esters, glycerin fatty acid esters, fatty acid polyglycerides, fatty acid alcohol polyglycol ethers, acetylene glycol, acetylene alcohol, oxyalkylene block polymers, polyoxyethylene alkyl ethers, polyoxyethylene alkyl aryl ethers, polyoxyethylene styryl aryl ethers, polyoxyethylene glycol alkyl ethers, polyoxyethylene fatty acid esters, polyoxyethylene sorbitan fatty acid esters, polyoxyethylene glycerin fatty acid esters, polyoxyethylene hydrogenated castor oil or polyoxypropylene fatty acid esters.

Examples of anti-freezing agents include, but are not limited to, ethylene glycol, diethylene glycol, propylene glycol and glycerin.

Examples of preservatives include, but are not limited to, benzoic acid, sodium benzoate, methyl paraoxybenzoate, butyl paraoxybenzoate, isopropyl methyl phenol, benzalkoniumn chloride, chlorhexidine hydrochloride, aqueous hydrogen peroxide, chlorhexidine gluconate, salicylic acid, sodium salicylate, zinc pyrithione, sorbic acid, potassium sorbate, dehydroacetic acid, sodium dehydroacetate, phenoxyethanol, isothiazoline derivatives such as 5-chloro-2-methyl-4-isothiazolin-3-one or 2-methyl-4-isothiazolin-3-one, 2-bromo-2-nitropropane-1,3-diol and salicylic acid derivatives.

The previously mentioned solid vehicles, liquid vehicles, binders, thickeners, surfactants, anti-freezing agents and preservatives can each be used alone or in a suitable combination thereof corresponding to the purpose of use and the like.

Although the incorporated ratio of the compound of formula (I) of the present invention with respect to the total herbicide composition of the present invention can be increased or decreased as necessary and there are no particular limitations thereon, it is normally about 0.01% by weight to 90% by weight, and for example, in the case of being in the form of a dustable powder or granules, is preferably about 0.1% by weight to 50% by weight and more preferably about 0.5% by weight to 10% by weight, while in the case of being in the form of an emulsifiable concentrate, wettable powder or water dispersible granules, is preferably about 0.1% by weight to 90% by weight and more preferably about 0.5% by weight to 50% by weight.

These preparations can be provided for use in various types of applications by diluting to a suitable concentration as necessary followed by spraying or applying directly to plant foliage, soil or the surface of a rice paddy and the like.

The following provides an explanation of the present invention through examples thereof.

EXAMPLES

Example 1: Method for the Synthesis of Methyl N-(1-(3-chloro-4,5,6,7-tetrahydropyrazolo[1,5-a]pyridin-2-yl)-4-cyanopyrazol-5-yl)-2-(2-fluorophenyl) Acetoamide (Compound 1)

Acetonitrile (5 ml) was added to 5-amino-1-(3-chloro-4,5,6,7-tetrahydropyrazolo[1,5-a]pyridin-2-yl)pyrazole-4-carbonitrile (1.3 g) followed by slowly dropping in (2-fluorophenyl)acetyl chloride (1.0 g) and heating to reflux for 8 hours. Following completion of the reaction, water was added to the reaction solution followed by extraction with ethyl acetate. After washing with an aqueous sodium bicarbonate solution and drying with sodium sulfate, the solvent was distilled off under reduced pressure. The resulting crude product was washed with isopropyl ether to obtain the desired compound (1.9 g).

The starting material in the form of the compound of formula (II) was synthesized in accordance with WO 93/10100 and WO 94/08999.

The examples listed in the following tables can be synthesized by the same manner as the above-mentioned methods or obtained in the same manner as the above-mentioned methods.

TABLE 1

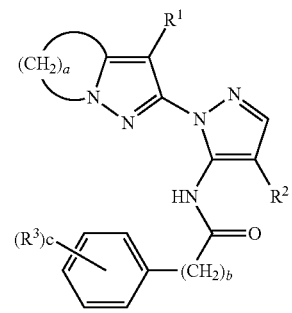

| Compound | R¹ | R² | (R³)c | a | b | mp | Refractive index (° C.) |
|---|---|---|---|---|---|---|---|
| 1 | Cl | CN | 2-fluoro | 4 | 1 | 173-174 | |
| 2 | Cl | CN | H | 3 | 1 | 169-170 | |
| 3 | Cl | CN | H | 4 | 1 | 144-145 | |
| 4 | Br | CN | H | 4 | 1 | 170 | |
| 5 | Cl | NO₂ | H | 4 | 1 | 124-125 | |
| 6 | Cl | CN | 2-methyl | 4 | 1 | 124-125 | |
| 7 | Cl | CN | 2-methoxy | 4 | 1 | 125 | |
| 8 | Cl | CN | 2-chloro | 4 | 1 | 170-171 | |
| 9 | Cl | CN | 3-methyl | 4 | 1 | 140 | |
| 10 | Cl | CN | 3-methoxy | 4 | 1 | 118-119 | |

TABLE 2

| Compound | R¹ | R² | (R³)c | a | b | mp | Refractive index (° C.) |
|---|---|---|---|---|---|---|---|
| 11 | Cl | CN | 3-fluoro | 4 | 1 | 156-157 | |
| 12 | Cl | CN | 3-chloro | 4 | 1 | 148-149 | |
| 13 | Cl | CN | 4-methyl | 4 | 1 | 175-176 | |
| 14 | Cl | CN | 4-methoxy | 4 | 1 | 135-136 | |
| 15 | Cl | CN | 4-fluoro | 4 | 1 | 163-164 | |
| 16 | Cl | CN | 4-chloro | 4 | 1 | 142-143 | |
| 17 | Cl | CN | 4-trifluoromethyl | 4 | 1 | 161-162 | |
| 18 | Cl | CN | 2,4-dichloro | 4 | 1 | 147-148 | |
| 19 | Cl | CN | H | 4 | 2 | 132-133 | |
| 20 | Cl | CN | 2-methyl | 4 | 2 | | |
| 21 | Cl | CN | 3-methyl | 4 | 2 | | |
| 22 | Cl | CN | 4-methyl | 4 | 2 | | |
| 23 | Cl | CN | 2-methoxy | 4 | 2 | | |
| 24 | Cl | CN | 3-methoxy | 4 | 2 | | |
| 25 | Cl | CN | 4-methoxy | 4 | 2 | | |
| 26 | Cl | CN | 2-fluoro | 4 | 2 | | |
| 27 | Cl | CN | 3-fluoro | 4 | 2 | | |
| 28 | Cl | CN | 4-fluoro | 4 | 2 | | |
| 29 | Cl | NO₂ | 2-methyl | 4 | 1 | | |
| 30 | Cl | NO₂ | 3-methyl | 4 | 1 | | |
| 31 | Cl | NO₂ | 4-methyl | 4 | 1 | | |
| 32 | Cl | NO₂ | 2-methoxy | 4 | 1 | | |
| 33 | Cl | NO₂ | 3-methoxy | 4 | 1 | | |
| 34 | Cl | NO₂ | 4-methoxy | 4 | 1 | | |
| 35 | Cl | NO₂ | 2-fluoro | 4 | 1 | | |
| 36 | Cl | NO₂ | 3-fluoro | 4 | 1 | | |
| 37 | Cl | NO₂ | 4-fluoro | 4 | 1 | | |

Preparation Examples

1. Dustable Powder

| | |
|---|---|
| Compound of formula (I) | 10 parts by weight |
| Talc | 90 parts by weight |

A dustable powder is obtained by mixing the above components and finely crushing with a hammer mill.

2. Wettable Powder

| | |
|---|---|
| Compound of formula (I) | 10 parts by weight |
| Polyoxyethylene alkyl aryl ether sulfate | 22.5 parts by weight |
| White carbon | 67.5 parts by weight |

A wettable powder is obtained by mixing the above components and finely crushing the mixture with a hammer mill.

3. Flowable Concentrate

| | |
|---|---|
| Compound of formula (I) | 10 parts by weight |
| Polyoxyethylene alkyl ether phosphate | 10 parts by weight |
| Bentonite | 5 parts by weight |
| Ethylene glycol | 5 parts by weight |
| Water | 70 parts by weight |

A flowable agent is obtained by mixing the above components and crushing using a wet pulverizer.

4. Emulsifiable Concentrate

| | |
|---|---|
| Compound of formula (I) | 15 parts by weight |
| Ethoxylated nonylphenol | 10 parts by weight |
| Cyclohexanone | 75 parts by weight |

An emulsifiable concentrate is obtained by mixing the above components.

5. Granules

| | |
|---|---|
| Compound of formula (I) | 5 parts by weight |
| Calcium lignin sulfonate | 3 parts by weight |
| Polycarboxylate | 3 parts by weight |
| Calcium carbonate | 89 parts by weight |

The above components are mixed followed by adding water, kneading, extruding and granulating. Subsequently, granules are obtained by drying followed by sizing.

Biological Testing Examples

1. Paddy Herbicidal Activity Test

Rice paddy soil was filled into a 1/10000 are pot followed by the addition of suitable amounts of water and chemical fertilizer, kneading, seeding with *Echinochloa crus-galli, Monochoria vaginalis* and *Scirpus juncoides* and maintaining in an irrigated state at a water depth of 3 cm.

Wettable powders of Target Compound (I) shown in Table 1 prepared in compliance with the preparation examples were diluted with a suitable amount of water, rice plants in the 2.0 leaf stage were transplanted during 3.5 leaf stage of *Echinochloa crus-galli*, and treated by dropping in chemical in the prescribed amount per 10 are using a pipette.

After treating for 30 days in a glass greenhouse at an average atmospheric temperature of 30° C., the herbicidal efficacy thereof was investigated.

Evaluation of herbicidal efficacy was carried out by comparing growth inhibition rate (%) with an untreated group, while evaluation of phytotoxicity was carried out by comparing growth inhibition rate (%) with the state of a complete eradication group, and were evaluated at 11 levels indicated below.

0 (exponent): 0% to less than 10% (growth inhibition rate)

1: 10% to less than 20%

2: 20% to less than 30%

3: 30% to less than 40%

4: 40% to less than 50%

5: 50% to less than 60%

6: 60% to less than 70%

7: 70% to less than 80%

8: 80% to less than 90%

9: 90% to less than 100%

10: 100%

The results are shown in Table 2.

Control agent 2.19 (described in WO 94/0899)

[Chemical formula 3]

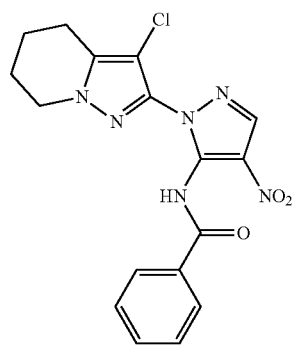

(2.19)

Control agent 4.192 (described in WO 94/08999)

[Chemical formula 4]

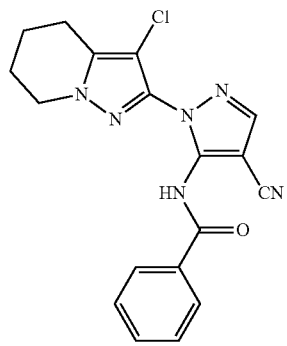

(4.192)

TABLE 2

| | 5g$^{a.i.}$/10a | | | | 1g$^{a.i.}$/10a | | | |
|---|---|---|---|---|---|---|---|---|
| Compound | Echinochloacrus-galli | Scirpus juncoides | Monochoria vaginalis | Oryzasativa | Echinochloacrus-galli | Scirpus juncoides | Monochoria vaginalis | Oryzasativa |
| 1 | 9 | 9 | 10 | 0 | 9 | 9 | 10 | 0 |
| 3 | 10 | 10 | 10 | 1 | 9 | 9 | 9 | 0 |
| 5 | 10 | 10 | 10 | 1 | 10 | 9 | 10 | 1 |
| 6 | 10 | 10 | 10 | 1 | 10 | 10 | 10 | 1 |
| 9 | 9 | 9 | 10 | 0 | 9 | 9 | 9 | 0 |
| 11 | 10 | 10 | 9 | 1 | 9 | 9 | 9 | 0 |
| 15 | 10 | 10 | 10 | 1 | 10 | 9 | 10 | 1 |
| 19 | 10 | 10 | 10 | 1 | 9 | 10 | 10 | 0 |
| 2.19 | 4 | 2 | 1 | 1 | 3 | 1 | 1 | 1 |
| 4.192 | 4 | 4 | 2 | 1 | 4 | 3 | 1 | 1 |

2. Farming Soil Treatment Test

Field soil was filled into a 1/6000 are pot followed by seeding with *Digitaria ciliaris, Chenopodium album* and *Amaranthus retroflexus* and covering with soil.

Wettable powders of compounds of formula (I) shown in Table 1 prepared in compliance with the preparation examples were diluted with water to the prescribed amount of chemical and uniformly sprayed onto each soil surface layer using 100 liters of sprayed water per 10 are prior to weed growth following seeding.

After treating for 30 days in a glass greenhouse at an average atmospheric temperature of 30° C., the herbicidal efficacy thereof was investigated.

Evaluation of herbicidal efficacy was carried out in the same manner as the above-mentioned Test Example 1.

The results are shown in Table 3.

3. Weed Foliar Treatment Test

Soil was filled into a 1/6000 are pot followed by seeding with *Digitaria ciliaris, Chenopodium album* and *Amaranthus retroflexus*, covering with soil, and cultivating in a glass greenhouse at an average atmospheric temperature of 25° C.

Wettable powders of Target Compound (I) shown in Table 1 prepared in compliance with the preparation examples were diluted with water to the prescribed amount of chemical and uniformly sprayed onto the weeds using 150 liters of sprayed water per 10 are when *Digitaria ciliaris* had grown to the 1.0 to 2.0 leaf stage.

After treating for 3 weeks in a glass greenhouse at an average atmospheric temperature of 25° C., the herbicidal efficacy thereof was investigated.

Evaluation of herbicidal efficacy was carried out in the same manner as the above-mentioned Test Example 1.

TABLE 3

| | 10g$^{a.i.}$/10a | | | 5g$^{a.i.}$/10a | | |
|---|---|---|---|---|---|---|
| Compound | Digitaria ciliaris | Chenopodium album | Amaranthus retroflexus | Digitaria ciliaris | Chenopodium album | Amaranthus retroflexus |
| 1 | 9 | 10 | 9 | 9 | 9 | 9 |
| 3 | 9 | 10 | 9 | 9 | 9 | 9 |
| 5 | 9 | 10 | 9 | 9 | 9 | 9 |
| 6 | 9 | 10 | 9 | 9 | 9 | 9 |
| 9 | 9 | 10 | 10 | 9 | 9 | 9 |
| 11 | 10 | 10 | 9 | 9 | 10 | 9 |
| 15 | 10 | 10 | 10 | 9 | 10 | 10 |
| 19 | 10 | 10 | 10 | 10 | 10 | 10 |
| 2.19 | 2 | 4 | 3 | 0 | 3 | 1 |
| 4.192 | 2 | 3 | 1 | 0 | 2 | 0 |

The results are shown in Table 4.

TABLE 4

| | 10g$^{a.i.}$/10a | | | 5g$^{a.i.}$/10a | | |
|---|---|---|---|---|---|---|
| Compound | Digitaria ciliaris | Chenopodium album | Amaranthus retroflexus | Digitaria ciliaris | Chenopodium album | Amaranthus retroflexus |
| 1 | 10 | 10 | 10 | 10 | 10 | 10 |
| 3 | 10 | 10 | 10 | 10 | 10 | 9 |
| 5 | 10 | 10 | 10 | 10 | 10 | 10 |
| 6 | 10 | 10 | 10 | 10 | 10 | 10 |
| 9 | 10 | 10 | 10 | 10 | 10 | 10 |
| 11 | 10 | 10 | 10 | 10 | 10 | 10 |
| 15 | 10 | 10 | 10 | 10 | 10 | 10 |
| 19 | 10 | 10 | 10 | 10 | 10 | 10 |
| 2.19 | 2 | 5 | 4 | 1 | 4 | 4 |
| 4.192 | 2 | 5 | 4 | 1 | 4 | 3 |

4. Weed Foliar Treatment Test

Field soil was filled into a 1/4500 are pot followed by seeding with *Digitaria ciliaris* and *Galinsoga parviflora*, covering with soil and cultivating in a glass greenhouse at an average atmospheric temperature of 25° C.

Wettable powders of Target Compound (I) shown in Table 1 prepared in compliance with the preparation examples were diluted with water to the prescribed amount of chemical and uniformly sprayed onto the weeds using 100 liters of sprayed water per 10 are when *Digitaria ciliaris* had grown to the 4.0 to 5.0 leaf stage (plant height: 10 cm to 15 cm).

After treating for 20 days in a glass greenhouse at an average atmospheric temperature of 25° C., the herbicidal efficacy thereof was investigated.

Evaluation of herbicidal efficacy was carried out in the same manner as the above-mentioned Test Example 1.

The results are shown in Table 5.

TABLE 5

| Compound | 10 $g^{a.i.}$/10 a | |
|---|---|---|
| | *Digitaria ciliaris* | *Galinsoga parviflora* |
| 1 | 10 | 10 |
| 2 | 10 | 10 |
| 3 | 10 | 10 |
| 4 | 10 | 10 |
| 5 | 10 | 10 |
| 6 | 10 | 10 |
| 7 | 10 | 10 |
| 8 | 10 | 10 |
| 9 | 10 | 10 |
| 10 | 10 | 10 |
| 11 | 10 | 10 |
| 12 | 10 | 10 |
| 13 | 10 | 10 |
| 14 | 10 | 10 |
| 15 | 10 | 10 |
| 16 | 10 | 10 |
| 17 | 10 | 10 |
| 18 | 10 | 10 |
| 19 | 10 | 10 |
| 2.19 | 1 | 3 |
| 4.192 | 0 | 2 |

INDUSTRIAL APPLICABILITY

According to the present invention, the compound for formula (I) of the present invention is useful as a herbicide against harmful plants since it has superior herbicidal efficacy against undesirable plants.

The invention claimed is:

1. A compound represented by the following formula (I):

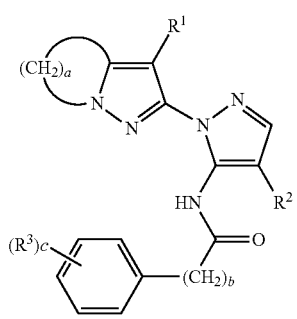

(I)

wherein, $R^1$ represents a chlorine atom or bromine atom, $R^2$ represents a cyano group or nitro group, $R^3$ represents a halogen atom, hydroxyl group, cyano group, nitro group, $C_1$-$C_4$ alkyl group which may be optionally substituted with one or more halogen atoms, or $C_1$-$C_4$ alkoxy group which may be optionally substituted with one or more halogen atoms, a represents 3 to 5, b represents 1 to 3, and c represents 1 to 5, and each $R^3$ may be mutually the same or different when c is 2 or more.

2. The compound according to claim 1, wherein $R^1$ represents a chlorine atom, $R^2$ represents a cyano group, a represents 4, b represents 1, and c represents 1.

3. A herbicide composition containing a herbicidally effective amount of at least one compound according to claim 1.

4. The herbicide composition according to claim 3, further containing a formulation assistant.

5. A method for controlling undesirable plants, said method comprising the step of applying an effective amount of at least one compound according to claim 1 to an undesirable plant or the location of the undesirable plant.

6. A herbicide composition containing a herbicidally effective amount of at least one compound according to claim 2.

7. The herbicide composition according to claim 6, further containing a formulation assistant.

8. A method for controlling undesirable plants, said method comprising the step of applying an effective amount of at least one compound according to claim 2 to an undesirable plant or the location of the undesirable plant.

9. A method for controlling undesirable plants, said method comprising the step of applying an effective amount of the herbicide composition according to claim 3 to an undesirable plant or the location of the undesirable plant.

10. A method for controlling undesirable plants, said method comprising the step of applying an effective amount of the herbicide composition according to claim 6 to an undesirable plant or the location of the undesirable plant.

11. A method for controlling undesirable plants, said method comprising the step of applying an effective amount of the herbicide composition according to claim 4 to an undesirable plant or the location of the undesirable plant.

12. A method for controlling undesirable plants, said method comprising the step of applying an effective amount of the herbicide composition according to claim 7 to an undesirable plant or the location of the undesirable plant.

* * * * *